United States Patent [19]

Gröninger

[11] 4,227,399
[45] Oct. 14, 1980

[54] APPARATUS FOR CONTACTING SAMPLES WITH WATER VAPORS

[76] Inventor: Kurd Gröninger, Büelstrasse 556, CH-5626 Lengnau, Switzerland

[21] Appl. No.: 969,651

[22] Filed: Dec. 15, 1978

[30] Foreign Application Priority Data

Dec. 27, 1977 [CH] Switzerland .................... 16039/77

[51] Int. Cl.³ .............................................. G01N 5/02
[52] U.S. Cl. .......................................... 73/76; 73/73; 116/209
[58] Field of Search .................. 73/73, 1 G; 116/209; 366/273; 76/76

[56] References Cited

U.S. PATENT DOCUMENTS

| | | | |
|---|---|---|---|
| 2,575,169 | 11/1951 | Green, Jr. ................................. | 73/73 |
| 2,635,459 | 4/1953 | Gray ...................................... | 73/73 X |
| 3,253,458 | 5/1966 | Katz et al. ............................... | 73/73 |
| 3,784,170 | 1/1974 | Peterson et al. ...................... | 366/273 |
| 3,788,128 | 1/1974 | Strohecker ............................. | 73/73 |
| 3,911,723 | 10/1975 | Ritter ..................................... | 73/1 G |
| 4,069,701 | 1/1978 | Baldauf et al. ......................... | 73/1 G |

Primary Examiner—Daniel M. Yasich
Attorney, Agent, or Firm—Peter K. Kontler

[57] ABSTRACT

Apparatus for contacting various samples with water vapors has a vessel which is sealable by a removable cover and contains an insert above a supply of liquid electrolyte. The insert has an annulus of sockets for containers each of which confines a different sample and can be sealed by a removable lid. A vertical shaft is mounted in the insert with minimal friction for rotary and axial movement and is driven by a stirring device which rotates a permanent magnet serving to rotate a permanent magnet or a magnetizable body which is secured to the shaft. The shaft carries an impeller which agitates the gas in the interior of the vessel while the lids are off the respective containers. The supply of electrolyte is agitated by a bar which is rotated by the magnet of the stirring device or which constitutes the magnet or magnetizable body on the shaft.

25 Claims, 6 Drawing Figures

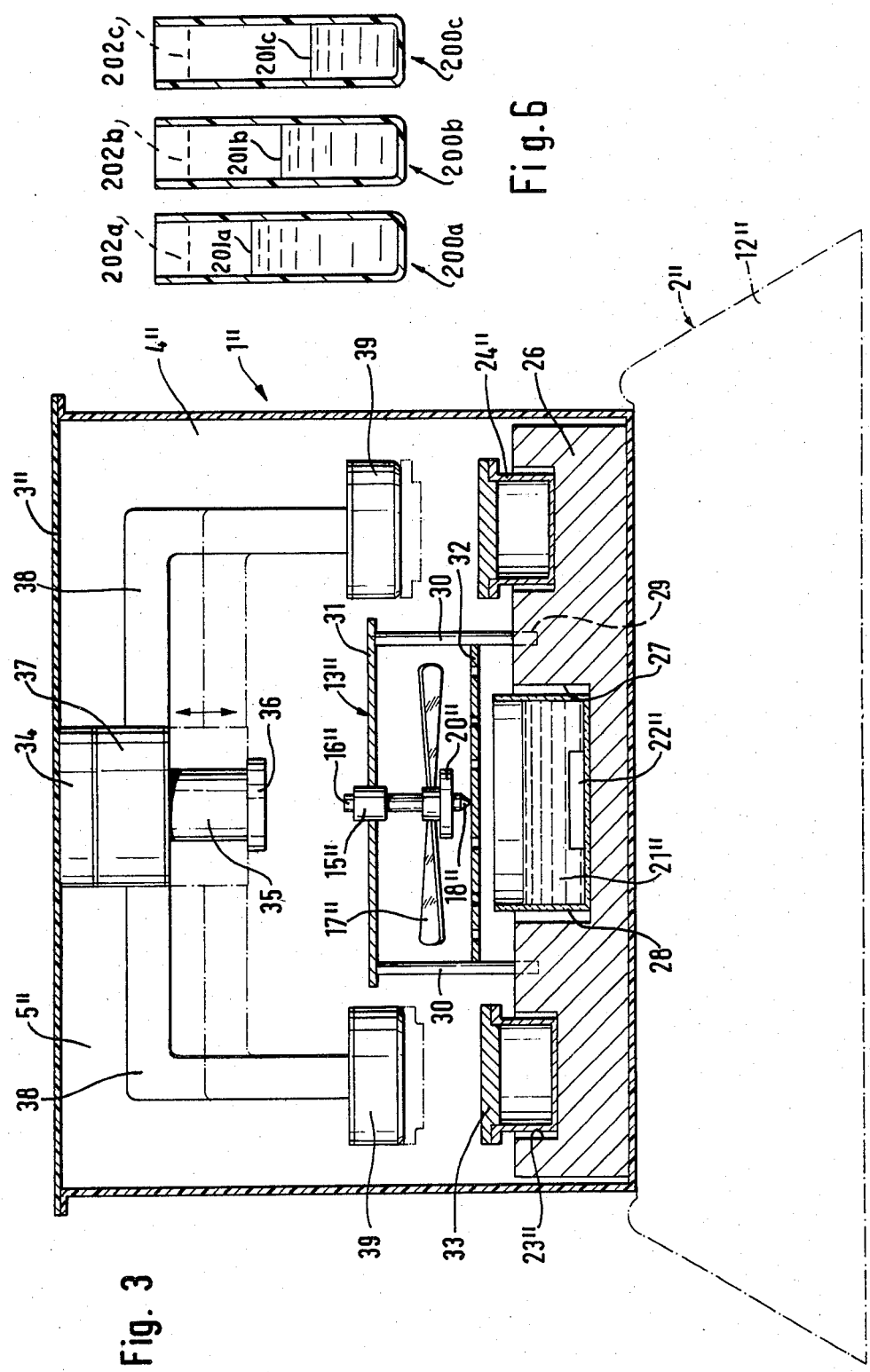

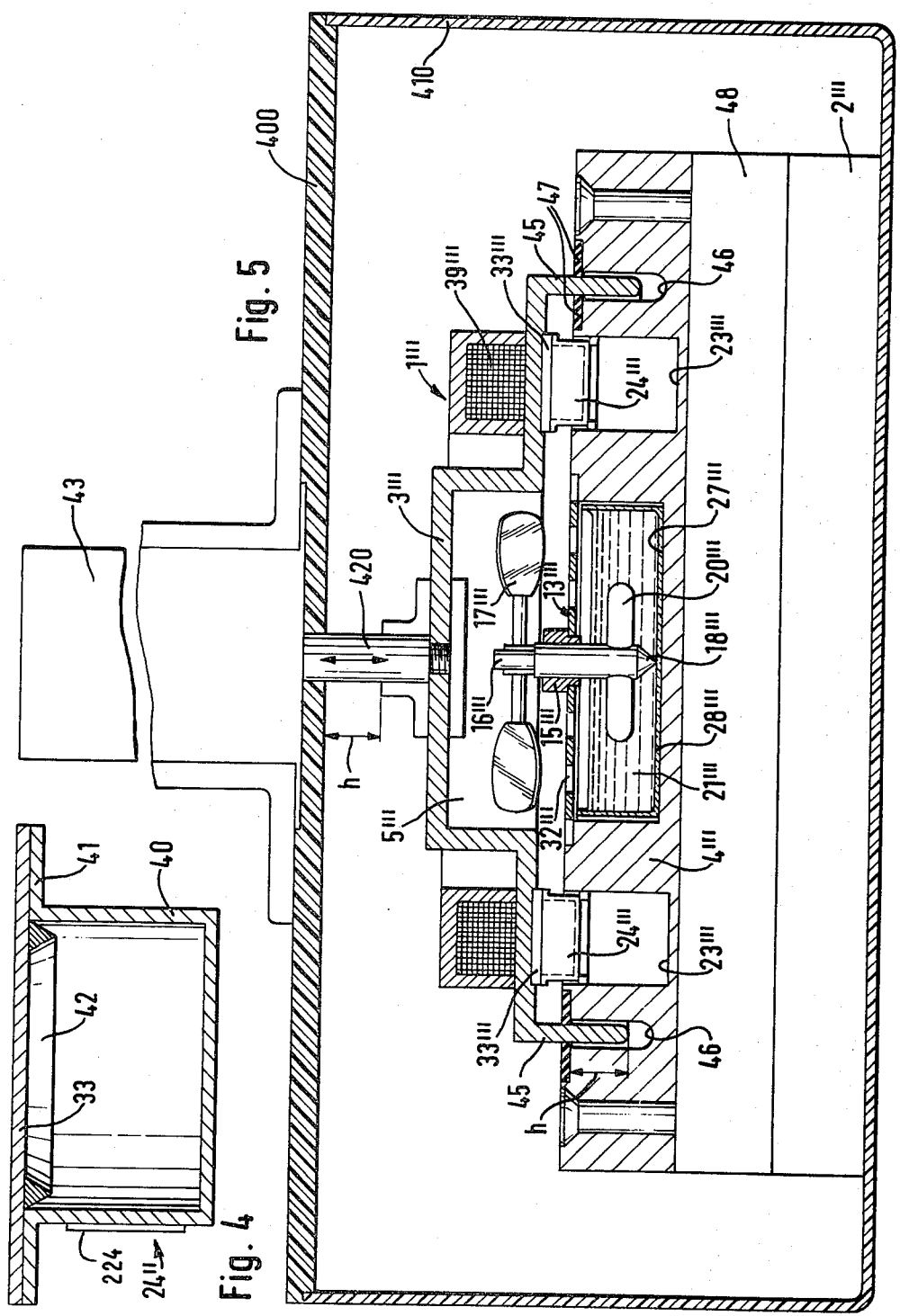

APPARATUS FOR CONTACTING SAMPLES WITH WATER VAPORS

BACKGROUND OF THE INVENTION

The present invention relates to apparatus for ascertaining sorption of water vapors by different samples which are confined in sealable containers. More particularly, the invention relates to apparatus for contacting various samples with water vapors under controlled circumstances to ascertain the maximum sorption of water vapors by the respective samples.

Heretofore known apparatus for contacting various samples with water vapors are bulky and expensive. Furthermore, each test is a time-consuming operation which must be performed or supervised by skilled persons.

OBJECTS AND SUMMARY OF THE INVENTION

An object of the invention is to provide a simple, compact and inexpensive apparatus which can be utilized for ascertainment of sorption of water vapors by a variety of substances, such as soil, foodstuffs, casting sand or concrete, either simultaneously or seriatim, and which can complete a test within an interval which is a fraction of the time required by resorting to heretofore known apparatus.

Another object of the invention is to provide a novel and improved exsiccator.

A further object of the invention is to provide an apparatus which can be utilized to ascertain absorption or desorption isotherms as well as practical isotherms of various substances.

An additional object of the invention is to provide a novel and improved method of producing various concentrations of humidity standards for use in an apparatus of the above outlined character.

Another object of the invention is to provide an apparatus which can be used for simultaneous testing of a substantial number of different samples or different quantities of a single substance.

A further object of the invention is to provide the apparatus with novel and improved means for maintaining the samples out of contact with the surrounding atmosphere.

One feature of the invention resides in the provision of an apparatus for measuring sorption of water vapors by a variety of samples. The apparatus comprises an exsiccator including a vessel which is sealable from the surrounding atmosphere and defines a space for water vapors, a supply of humidity standard for maintaining the percentage of water vapors in the space within the vessel at a predetermined value, at least one sample-confining container in the vessel, and means for agitating the contents of the space including a shaft, means for rotatably supporting the shaft with a minimum of friction, impeller means mounted on the shaft in the interior of the vessel, and means for rotating the shaft. The rotating means comprises a magnetic body on the shaft and means for transmitting torque to the shaft via the magnetic body, preferably in such a way that the torque transmitting means is not in direct contact with the shaft or with any part which shares the angular movements of the shaft. The shaft is preferably substantially vertical and is movable up and down with respect to the supporting means. The lower end portion of the substantially vertical shaft is preferably pointed, and the supporting means preferably includes a stationary abutment for the lower end portion of the shaft. At least the lower end portion of the shaft preferably consists of a synthetic plastic material. The supporting means for the shaft preferably includes an insert which is removably installed in the vessel, and the container may be removably installed in the insert. The insert may constitute a body of nonmagnetic heat-conducting material and may have a recess for the supply of humidity standard, e.g., an aqueous solution of sulfuric acid.

Another feature of the invention resides in the provision of a container which can receive samples and can be used in the above outlined apparatus. The container preferably comprises a substantially cup-shaped lower section having an open upper portion provided with an outwardly extending annular flange whose upper side constitutes a precision-finished smooth plane surface, and a lid which has a precision-finished plane underside movable into sealing contact with the upper side of the flange. The lid preferably consists, at least in part, of a magnetic or magnetizable material so that it can be lifted off or lowered onto the flange by resorting to a permanent magnet, an electromagnet or a combination of such magnets.

A further feature of the invention resides in the provision of a system of receptacles (e.g., ampules) having identical capacities and containing supplies of liquid electrolyte, such as sulfuric acid of predetermined concentration. By filling each of the receptacles to a different extent and by adding to the electrolyte water in such quantities that the combined volume of electrolyte and water in each receptacle is the same, one obtains a plurality of different humidity standards which can be used in the aforedescribed apparatus. For example, the capacity of each receptacle may be 50 ml.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 3 is a partly schematic central vertical sectional view of a third apparatus;

FIG. 4 is an enlarged central vertical sectional view of a container for samples which can be utilized in the improved apparatus;

FIG. 5 is a central vertical sectional view of a fourth apparatus; and

FIG. 6 illustrates three receptacles of a set of receptacles for the preparation of different humidity standards which can be used in the apparatus of the present invention.

DESCRIPTION OF THE PREFERRED EMBODIMENTS

Figure 1:
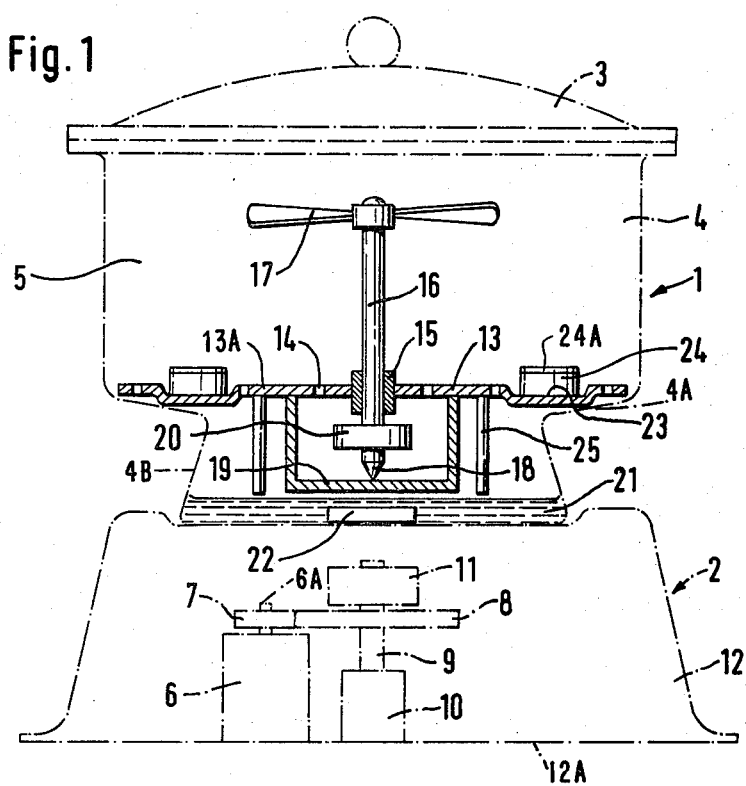
FIG. 1 is a partly schematic central vertical sectional view of an apparatus which embodies one form of the invention.

Referring to FIG. 1, there is shown an exsiccator 1 which is mounted on top of a magnetic driving device 2.

The exsiccator 1 comprises a detachable cover 3 for a vessel 4. When the cover 3 is properly applied, it fluid-tightly seals the internal space 5 of the vessel 4 from the surrounding atmosphere.

The driving device 2 comprises a housing 12 for an electric motor 6 whose vertical output element 6A drives a pinion 7 in mesh with a gear 8 which is secured to an upright shaft 9. The shaft 9 is rotatable in a bearing 10 which is mounted on a bottom wall 12A of the housing 12. The upper end portion of the shaft 9 is connected with and transmits torque to a permanent magnet 11. The housing 12 consists of nonmagnetic material.

In accordance with a feature of the invention, the apparatus of FIG. 1 further comprises an exsiccator insert 13 including a plate-like carrier 13A which is formed with a large number of holes 14 to constitute a horizontal sieve. The marginal portion of the sieve 13A rests on an internal shoulder 4A of the vessel 4 so that it is held in a horizontal plane. The central portion of the sieve 13A is provided with a sleeve-like bearing 15 which is secured thereto and surrounds a portion of a freely rotatable and axially movable shaft 16. The upper end portion of the shaft 16 is connected to and transmits torque to an impeller 17 which comprises one or more blades serving to agitate the gaseous contents of the internal space 5. The lower end portion of the shaft 16 has a pointed tip 18 which rests on the bottom wall of an abutment or cage 19. The latter is mounted at the underside of the sieve 13A. The shaft 16 preferably consists of a highly wear-resistant synthetic plastic material. The lower portion of this shaft (at a level above the pointed tip 18) is connected with a permanent magnet 20 or with a body of magnetizable material which cooperates with the permanent magnet 11 to rotate the shaft 16 and the impeller 17 when the circuit of the motor 6 is completed.

The lowermost part or extension 4B of the vessel 4 (below the shoulder 4A) contains a supply 21 of liquid electrolyte serving as a means for maintaining the relative moisture content in the space 5 at a constant value. A ferromagnetic stirring bar or rod 22 is supported by the bottom wall of the extension 4B at a level above the permanent magnet 11. This stirring element 22 is immersed in the supply 21 of electrolyte.

The upper side of the sieve 13A has an annulus of discrete recesses or sockets 23 (or a circumferentially complete groove). The center of this annulus is located on the axis of the shaft 16, and each socket 23 can receive a discrete container 24. Each container 27 has a precision-finished top surface and a closure or lid 24A which tightly seals its interior from the surrounding atmosphere. It is advisable and desirable to provide the containers 24 with suitable indicia (e.g., in different colors) to avoid a mixup of samples which are confined therein.

FIG. 1 further shows that the sieve 13A has three equally spaced projections or legs 25 which extend downwardly beyond the receptacle 19 so that, upon removal from the vessel 4, the entire insert 13 can be readily placed onto a table or the like.

In order to ascertain their moisture equilibrium, dry samples (e.g., foodstuffs, concrete, casting sand or soil) are placed into discrete containers 24 which are thereupon closed and sealed by the respective lids 24A. The thus closed and sealed containers 24 are inserted into the sockets 23 of the sieve 13A before or after the insert 13 is placed into the vessel 4. The lids 24A are thereupon removed, the cover 3 is sealingly mounted on the vessel 4, and the motor 6 of the driving device 2 is started. The permanent magnet 11 rotates and drives the permanent magnet or magnetizable body 20 as well as the stirring element 22. This results in intensive agitation and circulation of the gaseous atmosphere in the space 5 as well as of the liquid electrolyte (supply 21). Therefore, the apparatus rapidly establishes a water vapor equilibrium between the supply 21, the gaseous atmosphere in the space 5 and the samples in the containers 24. Once the equilibrium is established, the cover 3 is removed, the lids 24A are placed on top of the respective containers 24, and the entire insert 13 is removed from the vessel 4. The extent to which the samples have absorbed water vapors during contact with the contents of the vessel 4 is determined for each sample by resorting to a conventional gravimetric procedure.

Figure 2:
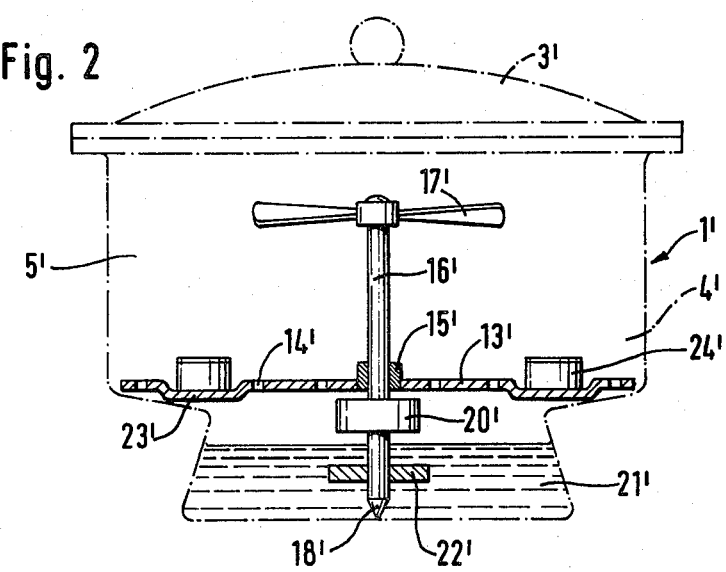
FIG. 2 is a similar partly schematic central vertical sectional view of the exsiccator of a modified apparatus.

FIG. 2 shows a portion of a modified apparatus wherein all such parts which are identical with or analogous to corresponding parts of the apparatus of FIG. 1 are denoted by similar reference characters each followed by a prime. The main difference is that the cage 19 of FIG. 1 is omitted and the tip 18' of the shaft 16' rests directly on the bottom wall 4D' of the extension 4B', i.e., this bottom wall constitutes an abutment for the lower end portion of the shaft 16'. The shaft 16' is somewhat longer than the shaft 16 of FIG. 1 so that its tip 18' dips into the supply 21' of electrolyte in the extension 4B'. The stirring element 22' need not consist of magnetic or magnetizable material because it is directly secured to and driven by the shaft 16'.

The operation of the apparatus of FIG. 2 is analogous to that of the first apparatus, i.e., the exsiccator 1' is placed onto a driving device corresponding to the device 2 of FIG. 1 so that the permanent magnet 11 of the device 2 rotates the shaft 16' via magnet 20' as soon as the circuit of the motor 6 is completed. The sieve 13A' of the insert 13' can be provided with legs (not shown in FIG. 2) corresponding to and serving the same purpose as the legs 25 shown in FIG. 1.

FIG. 3 illustrates a third apparatus wherein all such parts which are identical with or clearly analogous to corresponding parts of the apparatus of FIG. 1 are denoted by similar reference characters each followed by two primes. The exsiccator 1" comprises a vessel 4" which can be sealed by a cover 3" so that its internal space 5" cannot communicate with the surrounding atmosphere. The insert 13" in the vessel 4" comprises a block 26 consisting of a nonmagnetic heat-conducting material. This block rests on the bottom wall of the vessel 4" and its upper side is provided with sockets 23" for the containers 24". The central portion of the block 26 has a recess 27 for a glass tank 28 containing a supply 21" of liquid electrolyte. The tank 28 is readily removable from the recess 27. A ferromagnetic bar or rod 22" in the bottom portion of the tank 28 is rotated when the vessel 4" is placed onto the driving device 2" and the motor (not shown) in the housing 12" of the stirring device is started.

The upper side of the block 26 is further formed with three equidistant blind bores 29 which surround the recess 27 and receive the lower end portions of three upright posts 30 secured to and carrying a circular plate or table 31. The central portion of the table 31 is rigidly connected with a bearing sleeve 15" for a vertical shaft 16" which is freely rotatable and axially movable therein with a minimum of friction. The shaft 16" drives an impeller 17" which is located below the table 31 and a permanent magnet (or a magnetic body) 20″ which is mounted on the shaft 16″ between the impeller 17″ and the conical tip 18″. The tip 18″ rests on a sieve or abutment 32 which is secured to the posts 30 at a level above the open top of the tank 28. An advantage of the conical tip 18″ (and of the corresponding portions of the shafts 16 and 16′) is that the shaft 16″ can rotate with a minimum of friction.

When the motor of the stirring device 2″ is started, it drives the stirring element 22″ to agitate the supply 21″ of electrolyte in the tank 28. The device 2″ further rotates the shaft 16″ via permanent magnet (or magnetizable body) 20″ so that the impeller 17″ agitates the gaseous fluid in the space 5″ of the exsiccator 1″. The heat-conducting block 26 insures that the temperature of electrolyte in the tank 27 matches the temperature of samples in the containers 24″.

The lids 33 of the containers 24″ consist of a magnetizable material. A ring-shaped permanent magnet 34 which is secured to the underside of the central portion of the cover 3″ supports a downwardly extending vertical shaft 35 whose lower end portion constitutes a collar 36. The shaft 35 supports a vertically reciprocable electromagnet 37 which is movable between an upper end position (shown by solid lines) and a lower end position (indicated by phantom lines). By changing the polarity of the electromagnet 37, the latter is either attracted to or repelled from the permanent magnet 34. The two end positions of the electromagnet 37 are determined by the permanent magnet 34 and collar 36.

The electromagnet 37 carries radially outwardly extending inverted L-shaped arms 38 whose vertical portions extend downwardly toward the adjacent sockets 23″ in the upper side of the block 26. The free end portion of each arm 38 carries an electromagnet 39. The means for simultaneously energizing and deenergizing the electromagnets 39 is not specifically shown in the drawing.

When the electromagnet 37 is caused or allowed to assume its lower end position which is indicated by phantom lines, the electromagnets 39 are immediately adjacent to or contact the respective magnetizable lids 33. If the electromagnets 39 are thereupon energized and the electromagnet 37 is caused to move to the upper end position which is shown by solid lines, the electromagnets 39 lift the respective lids 33 off the corresponding containers 24″. The positions of two of the lids 33 in raised positions are indicated by phantom lines. The lids 33 are returned onto and seal the tops of the corresponding containers 24″ by lowering the electromagnet 37 and by thereupon deenergizing the electromagnets 39.

The operation of the apparatus of FIG. 3 is as follows:

The samples are introduced into the respective containers 24″ while the containers are located outside of the exsiccator 1″. The lids 33 are thereupon placed onto the respective containers 24″, the cover 3″ is lifted off the vessel 4″ and the filled, closed and sealed containers 24″ are inserted into the sockets 23″ of the block 26. The cover 3″ is returned to the illustrated position to seal the internal space 5″ from the surrounding atmosphere, and the electromagnet 37 is caused to move to its lower end position. The electromagnets 39 are energized and the electromagnet 37 is raised so that the lids 33 are lifted off the respective containers 24″. Thus, the exchange of moisture between the gaseous contents of the space 5″ and the samples in the uncovered containers 24″ can begin. When the equilibrium is reached, the electromagnet 37 is moved to its lower end position and the electromagnets 39 are deenergized so that the lids 39 seal the tops of the respective containers 24″. The cover 3″ is lifted off the vessel 4″ and the containers 24″, each with a lid 39 sealingly secured thereto, are removed from their sockets 23″. The apparatus of FIG. 3 insures that the exchange of moisture is terminated prior to lifting of the cover 3″, i.e., that the samples in the containers 24″ cannot exchange moisture with the surrounding atmosphere during removal of containers from the respective sockets 23″. The apparatus is then ready for renewed use, i.e., the sockets 23″ can receive containers 24″ with different samples.

The apparatus of FIG. 3 can be modified by utilizing a longer shaft 16″ whose tip 18″ comes to rest on the bottom wall of the glass tank 28. In such modified apparatus, the stirring element 22″ can be affixed to the shaft 16″.

The apparatus of FIG. 3 can be further modified by respectively replacing the parts 34 and 37 with an electromagnet and a permanent magnet. Still further, the permanent magnet 34 can be replaced with an electromagnet and the electromagnet 37 can be replaced with a hub consisting of ferromagnetic material. Such apparatus further comprises a helical spring which is interposed between the electromagnet (replacing the permanent magnet 34) and the hub (replacing the electromagnet 37) to move the hub to the lower end position (corresponding to the phantom-line position of the electromagnet 37) as soon as the electromagnet (replacing the permanent magnet 34) is deenergized.

FIG. 4 shows the details of a container 24″ for use in the apparatus of FIG. 3. The container 24″ comprises a nonmagnetic cylindrical lower section or cup 40 whose upper end is provided with an outwardly extending annular flange 41. The width of the flange 41 is preferably in the range of several (e.g., 3-5) millimeters, and the upper surface of the flange 41 is ground and polished or otherwise treated to a high degree of smoothness. The magnetizable closure or lid 33 has an outer diameter which is identical with the outer diameter of the flange 41, and the underside of the lid is finished to the same degree of smoothness as the upper side of the flange. The underside of the lid 33 is formed with a concentric centering rib 42 having a wedge-shaped cross-sectional outline to allow for convenient insertion into and centering in the top portion of the cup 40.

The reference character 224 denotes a label, plate or another suitable visually discernible indicium which identifies the illustrated container 24″. A different indicium is applied to each of a series of containers 24″ to facilitate rapid identification.

The apparatus of FIG. 5 comprises an exsiccator 1‴ and a magnetic stirring device 2‴. These parts are installed in a sealable insulating envelope or receptacle 410 having a detachable closure 400. The cover 3‴ for the vessel 4‴ of the exsiccator 1‴ is connected with a rod 420 which is reciprocable up and down in the closure 400 of the receptacle 410. A suitable motor 43 (e.g., a double-acting cylinder and piston unit) on the closure 400 is coupled to and can reciprocate the rod 420 to thereby lift or lower the cover 3‴. The stroke of the rod 420 is shown at h.

The cover 3‴ carries a ring-shaped electromagnet 39‴ which is coaxial therewith. The marginal portion of the cover 3‴ has a downwardly extending cylindrical portion 45 which is received in a circumferentially complete annular groove 46 of the vessel 4'''. The cylindrical portion 45 is engaged by two elastic sealing rings 47 which partially overlie the upper end of the groove 46 and are secured to the vessel 4'''. The extent of vertical movement of the cover 3''' (stroke h) is less than the axial length of the cylindrical portion 45 so that the portion 45 continues to extend into the groove 46 when the cover 3''' is held in the upper end position. Consequently, lifting of the cover 3''' does not result in communication between the internal space 5''' of the vessel 4''' and the surrounding atmosphere.

The vessel 4''' has a centrally located recess 27''' for a glass tank 28''' which contains a supply 21''' of liquid electrolyte. The insert 13''' is coaxial with the tank 28''' and has a perforated plate or sieve 32''' which overlies the tank 28'''. The sieve 32''' carries a coaxial bearing sleeve 15''' for a shaft 16''' which is rotatable and vertically movable therein. The shaft 16''' preferably consists of a synthetic plastic material and its lower end portion or tip is pointed, as at 18'''. This lower end portion or tip rests on an abutment which is the bottom wall of the tank 28'''. It will be noted that the axis of the shaft 16''' is normal to the plane of the bottom wall of the tank 28'''. The upper end portion of the shaft 16''' is connected with an impeller 17''', and the lower portion of this shaft (above the tip 18''') is connected with a permanent magnet 22''' which is a bar or rod extending diametrically of the shaft 16''' and dipping into the supply 21''' of liquid electrolyte in the tank 28'''. The permanent magnet 22''' constitutes a stirring element for the contents of the tank 28'''.

The vessel 4''' is further provided with several sockets 23''' which form an annulus surrounding the centrally located recess 27''' and each of which can receive a container 24'''. The bottom walls of the containers 24''' rest on annular shoulders 123''' in the respective sockets 23'''.

The apparatus of FIG. 5 further comprises a temperature regulating device 48 which preferably includes a copper plate located between the vessel 4''' and the stirring device 2'''. The copper plate 48 confines heating or cooling coils for a conditioning fluid whose temperature is maintained at a predetermined value by means of a thermostatically controlled heating or cooling device, not shown.

Prior to starting the motor of the driving device 2''', the containers 24''' are filled or partly filled with selected samples and each of these containers is then closed and sealed by a lid 33'''. The containers 24''' are thereupon inserted into the sockets 23'''. In the next step, the closure 400 (with the rod 420 held in the lower end position) is placed onto the receptacle 410 and the electromagnet 39''' is energized. The motor 43 is started to move the lid 3''' and the energized electromagnet 39''' upwardly through the distance h whereby the electromagnet 39''' lifts the lids 33''' off the respective containers 24''' so that the fluid in the space 5''' is free to contact the samples in the uncovered containers. The motor of the driving device 2''' is started to rotate the shaft 16''' via permanent magnet 22''' whereby the latter agitates the liquid of the supply 21''' and the impeller 17''' agitates the contents of the internal space 5'''. This insures that the moisture content of the gaseous medium is uniform in each and every part of the space 5'''. Thus, a moisture equilibrium can be established between the samples in the containers 24''' and the liquid electrolyte which constitutes the supply 21'''. Once such equilibrium is reached, the rod 420 is moved downwardly through the distance h and the electromagnet 39''' is deenergized so that the lids 33''' seal the tops of the respective receptacles 24'''. The closure 400 is lifted off the receptacle 410 so that the lid 33''' (which is removed with the closure 400) affords access to the closed and sealed containers 24'''. These containers can be removed in any desired sequence to be weighed in order to ascertain the moisture content of the samples therein by comparing the weight of containers 24''' prior to treatment with the weight of such containers subsequent to establishment of the equilibrium.

The apparatus of FIG. 5 exhibits the advantage that the internal space of the envelope or receptacle 410 constitutes a thermal seal between the exsiccator 1''' and the surrounding atmosphere when the closure 400 is held in the illustrated position.

In the embodiments of FIGS. 3 and 5, the electromagnets 39 of the ring-shaped electromagnet 39''' can be replaced with combinations of electromagnets and permanent magnets. The action of each permanent magnet is counter to that of the respective electromagnet. The permanent magnet attracts the respective lid 33 or the lids 33'''. When the associated electromagnet or electromagnets are energized, they overcome the force of the permanent magnet or magnets so that the lids 33''' or 33 are released and rest on the respective containers 24''' or 24.

It is preferred to employ a stirring device which comprises a relatively small motor (such as the motor 6 of FIG. 1) whose energy requirements are low. This insures that the driving device cannot heat (or exchanges only negligible quantities of heat energy with) the liquid electrolyte and/or the component parts of the exsiccator when the driving device is in use.

An important advantage of the improved apparatus is that the extent of sorption of water vapors by a variety of different samples can be determined in a time-saving operation. The apparatus is relatively simple, compact and inexpensive, and it can be used for simultaneous testing of a large number of samples. The results of tests can be used for ascertainment of absorption and desorption isotherms as well as for ascertainment of practical isotherms of one or more substances. Since the apparatus is relatively simple and inexpensive, several such apparatus can be set up in a laboratory for simultaneous testing of a very large number of samples, i.e., the low cost of improved apparatus renders it economically feasible to purchase and utilize several apparatus.

In order to evaluate the moisture equilibrium for a particular material, it is necessary to perform measurements of absorption of water vapors. The best known method of carrying such measurements is by resorting to an exsiccator. This involves placing a sample of the material to be examined into the exsiccator (i.e., into a gaseous atmosphere having a predetermined relative moisture content) until the state of equilibrium is reached. The aforementioned predetermined relative moisture content of the gaseous atmosphere is established and maintained by the electrolyte (also known as humidity standard) which is placed into the exsiccator. Such humidity standard is an aqueous electrolytic solution having a predetermined water activity, i.e., a predetermined partial water vapor pressure.

A presently preferred liquid electrolyte for use in exsiccators is diluted sulfuric acid. Several different liquid electrolytes or humidity standards are obtained by producing diluted sulfuric acids having different concentrations. This is achieved by resorting to tables and by utilizing piston type gauges, pipettes and similar instrumentalities. The water activity of each of the thus obtained series of acids is different. The production of such humidity standards is time-consuming as well as costly and must be carried out by skilled attendants. Therefore, another feature of the invention resides in the provision of novel and improved means for and method of producing different grades of liquid electrolyte in a time-saving manner and with a high degree of accuracy. The improved method renders it possible to produce humidity standards having any one of a wide range of different water activities.

To this end, one utilizes a set of receptacles, e.g., ampules, each containing a calibrated electrolyte solution for the production of humidity standards having different water activities. The arrangement is such that, by diluting the contents of an ampule to a certain extent (the diluting step includes the addition of water), one obtains one of several humidity standards. Prior to dilution, each ampule contains a different quantity of electrolyte, and the diluting step includes adding water in such quantity that the volume of dilute electrolyte in each of the ampules matches a predetermined value, i.e., each ampule receives a different quantity of diluent. In accordance with the invention, the capacities of all ampules are identical and each thereof contains a different quantity of liquid electrolyte having a preselected concentration. Thus, by the simple expedient of admitting into each ampule water in quantities which are needed to raise the volume of the thus diluted electrolyte, one obtains a series of different humidity standards whose water activity is known because the quantity of undiluted electrolyte is known.

In order to produce humidity standards whose water activity at 25° C. is

| 0.150 | 0.400 | 0.650 | 0.900 | 0.950 |
|-------|-------|-------|-------|-------|
| 0.200 | 0.450 | 0.700 | 0.910 | 0.960 |
| 0.250 | 0.500 | 0.750 | 0.920 | 0.970 |
| 0.300 | 0.550 | 0.800 | 0.930 | 0.980 |
| 0.350 | 0.600 | 0.850 | 0.940 | 0.990, | one can proceed as follows: Each of a set of twenty-five ampules has a capacity of 50 ml and each contains a different quantity of sulfuric acid with a concentration of 81 percent. The quantities (in ml) to obtain humidity standards according to the preceding table are as follows:

| 37.5 | 29.4 | 22.0 | 11.9 | 6.8 |
|------|------|------|------|-----|
| 35.6 | 27.8 | 20.4 | 10.3 | 5.8 |
| 33.8 | 26.5 | 18.5 | 9.5  | 4.6 |
| 32.3 | 25.1 | 16.5 | 8.7  | 3.2 |
| 30.8 | 23.6 | 14.1 | 7.8  | 1.7. |

It is clear that the ampules can be replaced with bottles consisting of a synthetic plastic material which is permeable to water vapors. Each of the ampules or bottles is filled to capacity by adding water to the aforementioned quantity of sulfuric acid. The water activity of humidity standards is then according to the first table.

It is further clear that ampules or bottles having a capacity of 50 ml merely constitute an example of component parts which can be used to produce a series of different humidity standards. Thus, one can employ larger or smaller ampules or bottles, and the concentration of liquid electrolyte prior to dilution with water can be higher or lower than 81 percent.

FIG. 6 shows, merely by way of example, three receptacles in the form of ampules 200a, 200b, 200c which are of identical size and shape. The upper levels of undiluted electrolyte in the ampules 200a-c are respectively shown at 201a, 201b, 201c, and the upper levels of humidity standards are shown at 202a, 202b, 202c (by broken lines). It will be noted that each ampule contains a different quantity of undiluted electrolyte and that the quantity of humidity standard in each ampule is the same.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for measuring sorption of water vapors by a variety of samples, comprising an exsiccator including a vessel defining a space having humidity standard liquid and vapor portions which is sealable from the surrounding atmosphere; means for maintaining the percentage of water vapors in said space at a predetermined value; at least one sample-confining container provided in the vapor portion in said space to absorb water vapors in said vessel; and means for agitating at least the vapor portion contents of said space, said agitating means including a shaft, means for rotatably supporting said shaft with a minimum of friction, impeller means mounted on said shaft in said vapor space, and means for rotating said shaft including a magnetic body on said shaft and means for selecting transmitting torque to said shaft via said magnetic body.

2. Apparatus as defined in claim 1, wherein said shaft is substantially vertical and is free to move up and down with respect to said supporting means.

3. Apparatus as defined in claim 2, wherein said shaft has a pointed lower end portion and said supporting means includes a stationary abutment for said lower end portion.

4. Apparatus as defined in claim 3, wherein at least said end portion of said shaft consists of synthetic plastic material.

5. Apparatus as defined in claim 3, wherein said exsiccator further comprises an insert in said vessel, said supporting means further comprising a sleeve bearing for said shaft and said abutment being secured to said insert below said bearing.

6. Apparatus as defined in claim 1, wherein said supporting means includes an insert removably installed in said vessel and having at least one socket, said container being disposed in and being removable from said socket.

7. Apparatus as defined in claim 6, wherein said maintaining means comprises the supply of liquid in said vessel and further comprising a stirring element driven by said shaft and dipping into said supply to agitate the liquid in response to rotation of said shaft.

8. Apparatus as defined in claim 7, wherein said shaft is substantially vertical and is movable up and down with respect to said insert.

9. Apparatus as defined in claim 6, wherein said insert has a plurality of sockets for discrete containers, said containers being provided with different visually discernible indicia.

10. Apparatus as defined in claim 6, wherein said insert further has apertures for circulation of fluids therethrough.

11. Apparatus as defined in claim 6, wherein said maintaining means comprises the supply of liquid in said insert.

12. Apparatus as defined in claim 11, wherein said insert has a recess for said supply of liquid.

13. Apparatus as defined in claim 6, wherein said insert includes a portion consisting of heat-conducting material, said socket being provided in said portion of said insert and said maintaining means comprising the supply of liquid in said portion.

14. Apparatus as defined in claim 13, wherein said material is nonmagnetic.

15. Apparatus as defined in claim 6, wherein said container comprises a lid of magnetizable material, and further comprising an electromagnet which is located above said socket and is energizable to attract the lid of a container in said socket, and means for moving said electromagnet up and down.

16. Apparatus as defined in claim 15, further comprising a removable cover for said vessel, said electromagnet being mounted on said cover and said moving means comprising means for moving said cover and said electromagnet with respect to said vessel, said cover being arranged to seal said space from the surrounding atmosphere in each position thereof.

17. Apparatus as defined in claim 16, further comprising a sealable insulating envelope for said vessel and said cover.

18. Apparatus as defined in claim 17, wherein said envelope comprises a closure and said moving means is mounted on said closure to move said cover up and down relative to said vessel.

19. Apparatus as defined in claim 1, wherein said maintaining means comprises the supply of humidity standard in said vessel and further comprising means for agitating said supply.

20. Apparatus as defined in claim 19, wherein said agitating means is said magnetic body and said body is connected to said shaft.

21. Apparatus as defined in claim 1, wherein said container comprises a lid of magnetizable material and further comprising means for lifting said lid off said container, including a permanent magnet which tends to maintain said lid on said container and an electromagnet which is energizable to lift said lid against the opposition of said permanent magnet.

22. Apparatus as defined in claim 1, said container comprising a substantially cup-shaped lower section having an upper end portion provided with an outwardly extending annular flange, said flange having a precision-finished smooth and plane upper surface, and a lid for said lower section, said lid having a precision-finished plane underside sealingly contacting said upper surface.

23. Apparatus as defined in claim 22, wherein the width of said flange is in the range of several millimeters.

24. Apparatus as defined in claim 22, wherein said lower section consists of nonmagnetic material and said lid consists of magnetic or magnetizable material.

25. Apparatus as defined in claim 22, wherein said lid comprises a downwardly extending centering portion in said lower section.

* * * * *